(12) United States Patent
Crabtree et al.

(10) Patent No.: US 9,730,590 B2
(45) Date of Patent: *Aug. 15, 2017

(54) SYSTEM OR METHOD FOR ASSESSING A SUBJECT'S PERIPHERAL BLOOD CIRCULATION

(71) Applicant: Dialog Devices Limited, Loughborrough, Leicestershire (GB)

(72) Inventors: Vincent Peter Crabtree, Loughborough (GB); Peter Richard Smith, Griffydam (GB)

(73) Assignee: Dialog Devices Limited, Loughborough, Leicestershire (GB)

( * ) Notice: Subject to any disclaimer, the term of this patent is extended or adjusted under 35 U.S.C. 154(b) by 0 days.

This patent is subject to a terminal disclaimer.

(21) Appl. No.: 14/049,366

(22) Filed: Oct. 9, 2013

(65) Prior Publication Data

US 2014/0039326 A1    Feb. 6, 2014

Related U.S. Application Data

(63) Continuation of application No. 10/584,179, filed as application No. PCT/GB2005/000051 on Jan. 5, 2005, now Pat. No. 8,585,602.

(30) Foreign Application Priority Data

Jan. 8, 2005 (GB) .................................. 0400281.2

(51) Int. Cl.
*A61B 5/02* (2006.01)
*A61B 5/026* (2006.01)
(Continued)

(52) U.S. Cl.
CPC .............. *A61B 5/02* (2013.01); *A61B 5/0261* (2013.01); *A61B 5/0295* (2013.01); *A61B 5/6829* (2013.01)

(58) Field of Classification Search
CPC .............. A61B 5/02007; A61B 5/0295; A61B 2560/0261
(Continued)

(56) References Cited

U.S. PATENT DOCUMENTS 4,036,215 A    7/1977 Doll ............................... 600/505
4,569,355 A    2/1986 Bitterly ......................... 128/691
(Continued)

FOREIGN PATENT DOCUMENTS

DE    37 44 538 A1    7/1989
DE    197 07 442 A1    8/1998
(Continued)

OTHER PUBLICATIONS

Vegfors, et al. "The influence of changes in blood flow on the accuracy of pulse oximetry in humans." May 1992. Acta Anaesthesiol Scand. 36(4): 346-9.*
(Continued)

*Primary Examiner* — Navin Natnithithadha
*Assistant Examiner* — Eric Messersmith
(74) *Attorney, Agent, or Firm* — Harrington & Smith

(57) ABSTRACT

A system for assessing blood circulation in a subject's limb, including detection means for detecting a signal dependent upon the arterial blood volume in a limb of the subject when the subject is in a first posture and also when the subject is in a second posture, different to the first posture; and processing means for calculating a quantitative indicator that is dependent upon the ratio of the signal for the first posture to the signal for the second posture.

12 Claims, 2 Drawing Sheets

(51) Int. Cl.
*A61B 5/0295* (2006.01)
*A61B 5/00* (2006.01)

(58) Field of Classification Search
USPC ............... 600/323–340, 481–483, 500–507
See application file for complete search history.

(56) References Cited

U.S. PATENT DOCUMENTS

| | | | |
|---|---|---|---|
| 4,836,212 A | 6/1989 | Schmitt et al. | 128/667 |
| 5,040,540 A | 8/1991 | Sackner | 600/485 |
| 5,137,023 A | 8/1992 | Mendelson et al. | 128/633 |
| 5,237,994 A | 8/1993 | Goldberger | 128/633 |
| 5,291,895 A | 3/1994 | McIntyre | 600/485 |
| 5,361,769 A | 11/1994 | Nilsson | 128/666 |
| 5,365,924 A | 11/1994 | Erdman | 128/633 |
| 5,437,275 A | 8/1995 | Amundsen | 128/633 |
| 5,542,421 A | 8/1996 | Erdman | 600/477 |
| 5,638,593 A | 6/1997 | Gerhardt et al. | 29/592.1 |
| 5,730,136 A | 3/1998 | Laufer et al. | 128/661.08 |
| 5,778,879 A | 7/1998 | Ota et al. | 600/485 |
| 5,842,982 A | 12/1998 | Mannheimer | 600/340 |
| 5,991,648 A | 11/1999 | Levin | 600/344 |
| 5,991,654 A | 11/1999 | Tumey et al. | 600/479 |
| 6,047,201 A | 4/2000 | Jackson, III | 600/344 |
| 6,334,065 B1 | 12/2001 | Al-Ali et al. | 600/323 |
| 6,470,199 B1 | 10/2002 | Kopotic et al. | 600/344 |
| 6,589,171 B2 | 7/2003 | Kerisbilck | 600/300 |
| 2001/0037058 A1 | 11/2001 | Stone | 600/323 |
| 2002/0161291 A1* | 10/2002 | Kianl et al. | 600/324 |
| 2003/0163033 A1* | 8/2003 | Dekker | 600/323 |

FOREIGN PATENT DOCUMENTS

| | | |
|---|---|---|
| DE | 1 97 41 982 A1 | 10/1998 |
| EP | 0 282 210 A1 | 9/1988 |
| EP | 0 293 504 | 12/1988 |
| EP | 0 335 356 | 10/1989 |
| EP | 0 481 612 A1 | 4/1992 |
| EP | 0 572 684 A1 | 12/1993 |
| EP | 1 121 049 | 8/2001 |
| EP | 1 233 697 | 8/2002 |
| EP | 1 322 216 | 7/2003 |
| EP | 0 959 757 B1 | 5/2004 |
| EP | 1 558 134 | 8/2005 |
| GB | 1185443 | 3/1968 |
| GB | 2 394 178 A | 4/2004 |
| GB | 2 402 472 A | 12/2004 |
| JP | 04-259447 A | 9/1992 |
| WO | WO 95/02358 | 1/1995 |
| WO | WO 98/17174 | 4/1998 |
| WO | WO 00/21433 | 4/2000 |
| WO | WO 00/74562 A1 | 12/2000 |
| WO | WO 01/24845 | 4/2001 |
| WO | WO 01/24845 A3 | 4/2001 |
| WO | WO 01/41634 A2 | 6/2001 |
| WO | WO 02/28274 A1 | 4/2002 |
| WO | WO 03/080152 A2 | 3/2003 |
| WO | WO 03/094729 A1 | 11/2003 |
| WO | WO 2004/041079 A2 | 4/2004 |

OTHER PUBLICATIONS

Rathgeber et al. Influence of different types of recovery positions on perfusion indices of the forearm. Resuscitation. 1996.32: 13-17.*
Coffman et al: "Intermittent Claudication and rest pain: Physiologic concepts and therapeutic approaches", vol. 22, No. 1, Jul. 1, 1979, XP023061850.
Vegfors, et al. "The influence of changes in blood flow on the accuracy of pulse oximetry in humans." May 1992, Acta Anaesthesiol Scand. 36(4): 346-349.
Kim, et al. "Pulse Oximetry and Circulatory Kinetics Associated with Pulse Volume Amplitude Measured by Photoelectric," 1986, Anesth Analg, 65: 1333-1339.
Nasimi, et al., "Periodic posture stimulation of the baroreceptors and the local vasomotor reflexes," Journal of Biomedical Engineering, 1994 14(4): 307-312.

* cited by examiner

SYSTEM OR METHOD FOR ASSESSING A SUBJECT'S PERIPHERAL BLOOD CIRCULATION

CROSS REFERENCE TO RELATED APPLICATION

This is a continuation patent application of co-pending application No. 10/584,179 filed Apr. 17, 2007, which is a National Stage Application of International Application No. PCT/GB2005/000051 filed Jan. 10, 2005, which is hereby incorporated by reference in its entirety.

FIELD OF THE INVENTION

Embodiments of the invention relate to assessing a subject's peripheral blood circulation, in particular, but not exclusively, arterial blood flow to the foot.

BACKGROUND TO THE INVENTION

Healthy peripheral circulation is an important factor in quality of life, independent living and personal freedom. Disorders of the vascular system can arise from a number of diseases such as, for example, diabetes, arteriosclerosis, Reynard's syndrome, atherosclerosis.

There are a few clinic/GP based technologies that are used currently to assess peripheral blood circulation. However, these technologies are generally interpretive and must be practised by a correctly trained person.

BRIEF DESCRIPTION OF THE INVENTION

It would be desirable to provide for the objective assessment of peripheral blood circulation.

According to one aspect of the invention, there is provided a system for assessing blood circulation in a subject's limb, comprising: detection means for detecting a signal dependent upon the arterial blood volume in a limb of the subject when the subject is in a first posture and also when the subject is in a second posture, different to the first posture; and processing means for calculating a quantitative indicator that is dependent upon the ratio of the signal for the first posture to the signal for the second posture.

According to this aspect of the invention, there is provided a method for assessing blood circulation in a subject's limb, comprising: detecting a signal dependent upon the arterial blood volume in a limb of the subject when the subject is in a first posture; detecting the signal dependent upon the arterial blood volume in the limb of the subject when the subject is in a second posture, different to the first posture; and calculating a quantitative indicator that is dependent upon the ratio of the signal for the first posture to the signal for the second posture.

The signal may be a pulsating (arterial) component of a measured parameter, the measured parameter being dependent upon the blood volume in the subject's limb.

The signal may be dependent upon the volume of arterial blood in the limb and other subject specific factors. The ratio of signals at different postures eliminates the subject specific factors and provides an objective indicator.

The measured parameter may, for example, be the intensity of light reflected from the limb. The intensity of the reflected light may be modeled as an attenuation of the intensity of incident light by a first exponential factor and a second exponential factor. The first exponential factor has a first exponent that represents the light absorption by arterial blood of the subject. The second exponential factor has a second exponent that represents the light absorption by other factors including venous blood for the subject. According to this model, rapid variations in the measured parameter arise from the first exponent. The first exponent is very small and the first exponential factor can therefore be represented mathematically as a first order polynomial (i.e. 1+first exponent). A good approximation of the first exponent may be obtained, for example, by taking the ratio of the ac component of the measured parameter to the dc component of the measured parameter. Also according to this model, the first exponent comprises a factor that represents the light absorbency of the subject's arterial blood and a factor that represents the volume of the subject's arterial blood. According to this model, as the light absorbency of a subject's arterial blood remains constant between postural changes, then the ratio of the first exponent for a first posture to the first exponent for a second posture gives a 'pure' ratio of arterial volumes without other factors. This ratio can therefore be used as an objective quantitative indicator.

According to another aspect of the Invention, there is provided a system for assessing a subject's peripheral blood circulation, comprising: measurement means for measuring a parameter dependent upon the blood volume in a limb of the subject when the subject is in a first posture and also when the subject is in a second posture, different to the first posture; means for separating the parameter into a first component and a second component; and processing means for calculating a quantitative indicator wherein the calculation takes as inputs the first component of the parameter for the first posture and the first component of the parameter for the second posture.

According to this aspect of the invention, there is provided a method for assessing a subject's peripheral blood circulation, comprising: measuring a parameter dependent upon the blood volume in a limb of the subject when the subject is in a first posture and also when the subject is in a second posture, different to the first posture; separating the parameter into a first component and a second component; and processing means for calculating a quantitative indicator wherein the calculation takes as inputs the first component of the parameter for the first posture and the first component of the parameter for the second posture.

Typically, the first component is a pulsating component and the second component is non-pulsating component. The indicator may be dependent upon the ratio of the first component of the parameter for the first posture to the first component of the parameter for the second posture.

The first component of the parameter may be dependent upon the volume of arterial blood in the limb and other subject specific factors. The use of first components at different postures may be used to eliminate the subject specific factors and provide an objective indicator.

According to another aspect of the invention there is provided a system for assessing a subject's peripheral blood circulation, comprising: measurement means for measuring a parameter dependent upon the blood volume in a limb of the subject when the subject is in a first posture; means for separating the parameter into a first component and a second component; and processing means for calculating a quantitative indicator wherein the calculation takes as inputs the first component of the parameter for the first posture and the second component of the parameter for the first posture.

According to this aspect of the invention there is provided a method for assessing a subject's peripheral blood circulation, comprising: measuring a parameter dependent upon the blood volume in a limb of the subject when the subject is in a first posture; separating the parameter into a first component and a second component; and calculating a quantitative indicator wherein the calculation takes as inputs the first component of the parameter for the first posture and the second component of the parameter for the first posture.

The measured parameter may, for example, be the intensity of light reflected from the limb. The intensity of the reflected light may be modeled as an attenuation of the intensity of incident light by a first exponential factor and a second exponential factor. The first exponential factor has a first exponent that represents the light absorption by arterial blood of the subject. The second exponential factor has a second exponent that represents the light absorption by other factors including venous blood for the subject. According to this model, rapid variations in the measured parameter arise from the first exponent. The first exponent is very small and the first exponential factor can therefore be represented mathematically as a first order polynomial (i.e. 1+first exponent). A good approximation of the first exponent may be obtained by, for example, taking the ratio of the ac component of the measured parameter to the dc component of the measured parameter. Also according to this model, the first exponent comprises a factor that represents the light absorbency of the subject's arterial blood and a factor that represents the volume of the subject's arterial blood.

According to a further aspect of the invention there is provided a system for assessing blood circulation in a subject's limb, for example a foot, comprising: measurement means operable to measure a parameter indicative of the blood volume of the subject's limb when the subject is in a first posture and to measure the parameter when the subject is in a second posture and comprising means for isolating a variable value, of the measured parameter; processing means for determining a quantitative indictor that is dependent upon the ratio of the variable value of the parameter measured for the first posture to the variable value of the parameter measured for the second posture.

According to this further aspect of the invention there is provided a method for assessing blood circulation in a subject's limb, comprising: measuring a parameter indicative of the blood volume of the subject's limb when the subject is in a first posture; isolating a time-variable value of the parameter measured for the first posture; measuring the parameter indicative of the blood volume of the subject's limb when the subject is in a second posture; isolating a time-variable value of the parameter measured for the second posture; and determining a quantitative indictor that is dependent upon the ratio of the variable value of the parameter measured for the first posture to the variable value of the parameter measured for the second posture.

Embodiments of the invention therefore provide a quantitative indicator in a robust and quick manner at modest cost without discomfort to the user. Some embodiments may be automated,

BRIEF DESCRIPTION OF THE DRAWINGS

For a better understanding of the present invention reference will now be made by way of example only to the accompanying drawings in which.

DETAILED DESCRIPTION OF EMBODIMENTS OF THE INVENTION

The Figures illustrate a system 10 for assessing blood circulation in a subjects limb, comprising: detection means for detecting a signal dependent upon the arterial blood volume in a limb of the subject when the subject is in a first posture and also when the subject is in a second posture, different to the first posture; and processing means 5 for calculating a quantitative indicator that is dependent upon the ratio of the signal for the first posture to the signal for the second posture.

The blood volume in a lower limb includes a variable volume, and a fixed volume. The variable blood volume arises from pulsating blood flow within the arteries of the lower limb and varies with a periodicity in the range 0.5-3 Hz. The fixed volume includes the venous volume of blood and varies, if at all, over a time scale of several seconds.

The blood circulation system is governed in part by forces exerted by gravity. In order that a suitable blood flow is maintained throughout the body, the vascular system can adjust to any local pressure changes resulting from postural changes. Thus the resistance of the peripheral vascular system in the feet is high when a subject is standing compared with when they are supine. Although the relationships between pressure, flow and blood volume are complex, certain patterns can be identified that characterise the response of the circulation system to specific changes (e.g. postural changes). These patterns can be disrupted when a pathology is present such as an arterial blockage or when the vasculature has a reduced capability to respond to changes imposed upon it. This is the principle of response testing which is exploited in this invention.

When a lower limb is raised above the heart, the circulation system will respond to the change in localised blood pressure in a manner characteristic of any pathology. This characteristic change is detected by measuring changes in the blood volume in the limb.

Figure 1:
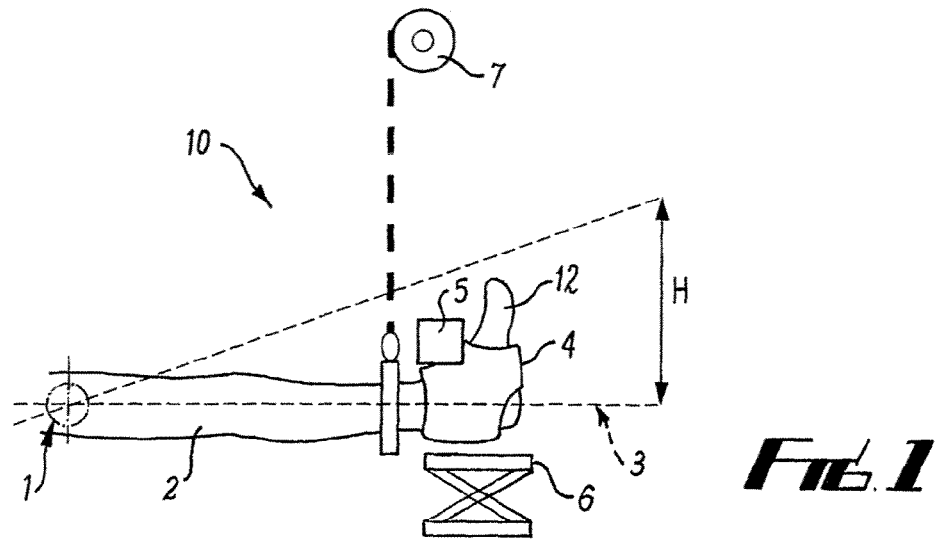
FIG. 1 schematically illustrates a system 10 for the objective assessment of blood perfusion in a lower limb 12 of a subject.

FIG. 1 schematically illustrates a system 10 for the objective assessment of blood perfusion in a lower limb 12 of a subject. The system 10 automatically determines quantitative indicators of lower limb blood perfusion and provides these perfusion indicators and/or an assessment of the subject's risk of vascular disorders. One perfusion indicator is obtained by measuring the change in pedal arterial circulation volume in a lower limb 12 in response to its elevation H above the subject's heart. Another indicator is obtained by measuring a change in the lower limb 12 flesh tone (colour) in response to its elevation H above the subject's heart.

The subject lies flat on their back, while a measurement is taken with the subject's lower limb 12 in a non-elevated position and a measurement is taken with the subject's lower limb 12 in an elevated position. Elevation is relative to the subject's heart reference level 3.

The system 10 comprises a lifting mechanism for raising a subject's leg 2 from the non-elevated position to the elevated position. The leg 2 pivots about the subject's hip 1. The mechanism may be a lifting pulley 7 or alternatively a lifting platform 6.

The system additionally comprises a blood volume sensor 4 and a control unit 5. The sensor 4 includes a support that fits around the lower limb 12, specifically around the ankle and dorsum of the foot. The sensor 4 may include a strain gauge wrapped around the dorsum or alternatively it may include a light source and light sensors to detect blood volume changes.

The control unit 5 receives a first input from the sensor when the subject is in a first posture e.g. the foot has a first zero elevation above the subject's heart and a second input from the sensor when the subject is in a second posture e.g. the foot has a second non-zero elevation above the subject's heart. The control unit 5 processes the first and second inputs to quantify the change in arterial blood volume with postural change. This may be used as a quantitative perfusion indicator that indicates the status of arterial blood circulation in the foot 12.

It may be desirable for the second input to be taken when the subject's foot 12 is at a particular elevation. The lifting mechanism may be calibrated to enable the foot to be manually elevated to the correct height. Alternatively, the lifting mechanism may provide a signal to the control unit 5, which automatically controls the lifting mechanism to stop elevation at a desired height or provides an alert to an operator to stop elevating the foot at the required height.

Instead of using the lifting mechanism to measure the elevation, it is also possible to use the control unit 5 to estimate the elevation. In this case, an electronic inclinometer would be attached to the subject's lower limb with a correct orientation. It may, for example, be integrated into the sensor 4 or control unit 5. The inclinometer provides an incline input θ to the control unit 5 which uses a value of the subject's leg length L to estimate the elevation H of the lower limb 12 using trigonometry (H=L*tan θ). The leg length L may be input into the control unit 5 after direct measurement or may be estimated by the control unit 5 from a value of the subject's height input to the control unit 5. The control unit 4 may additionally either control the rate of change of elevation by controlling the lifting mechanism or may monitor the rate of change of elevation and provide an audio alert if the rate of elevation is too fast or too slow.

In the illustrated embodiment, the control unit 5 forms part of the sensor support 4, but in other embodiments it may be mounted on the sensor support and directly connected to it or it may be positioned remote from the sensor support 4 and indirectly connected to it e.g. using radio transceivers.

The control unit 5 may include a user interface including a user input device such as a keyboard and a user output device such as a display. The display may, for example, display the elevation of the lower limb 12, the equivalent hydrostatic pressure for that elevation, a first perfusion indicator dependent upon the pedal arterial circulation volume in the elevated lower limb 12 and a second perfusion indicator dependent upon the flesh tone (colour) of the elevated lower limb.

Figure 2:
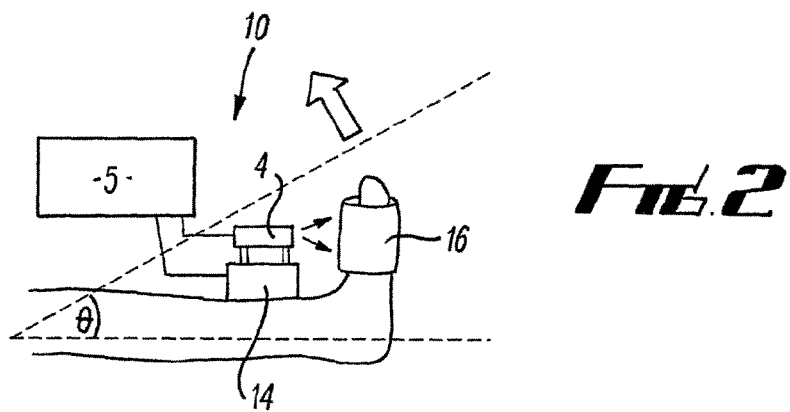
FIG. 2 illustrates a system 10 for the objective assessment of blood perfusion in a lower limb 12 of a subject using an optical sensor 4.

FIG. 2 illustrates a system 10 for the objective assessment of blood perfusion in a lower limb 12 of a subject using an optical sensor 4. The Figure illustrates a non-contact embodiment.

The system 10 comprises a photo-plethysmographic (PPG) 4 sensor, an electronic inclinometer (INC) 14, an optically diffusive skin (ODS) 16 and an electronic control unit (ECU) 5 that includes pre-processing circuitry 60 and an analysis unit (ANU) 56, which may be a microprocessor.

The PPG sensor 4 illuminates the dorsum of the foot from a range of a few cm. The PPG sensor 4 uses an array of light emitting diodes to provide a diffuse illumination pattern that extends over a significant fraction of the dorsum (approx. 20 sq cm). The optical receiver is located adjacent to the array of photodiodes or is mounted within the array. Light collection optics (reflectors or lenses) can be used to shape the beam pattern and collection aperture.

The optically diffusive skin (ODS) 16 covers the area of tissue to be illuminated (e.g. dorsum of the foot). The skin may, for example, be made from a polymer material such as latex. The skin 16 functions to reduce in-homogeneity in the optical interaction with the tissue by creating a smooth but diffusive interface between the illuminating light field and the actual skin surface.

The inclinometer 14 is aligned with the shinbone. The inclinometer 14 registers the angle θ at which the leg 2 is inclined. This value is converted to an elevation and hydrostatic pressure change by the electronic control unit 5. The leg length may be entered directly to the control unit 4 via or it may be derived from a look up table based on the subject's height.

Figure 3:
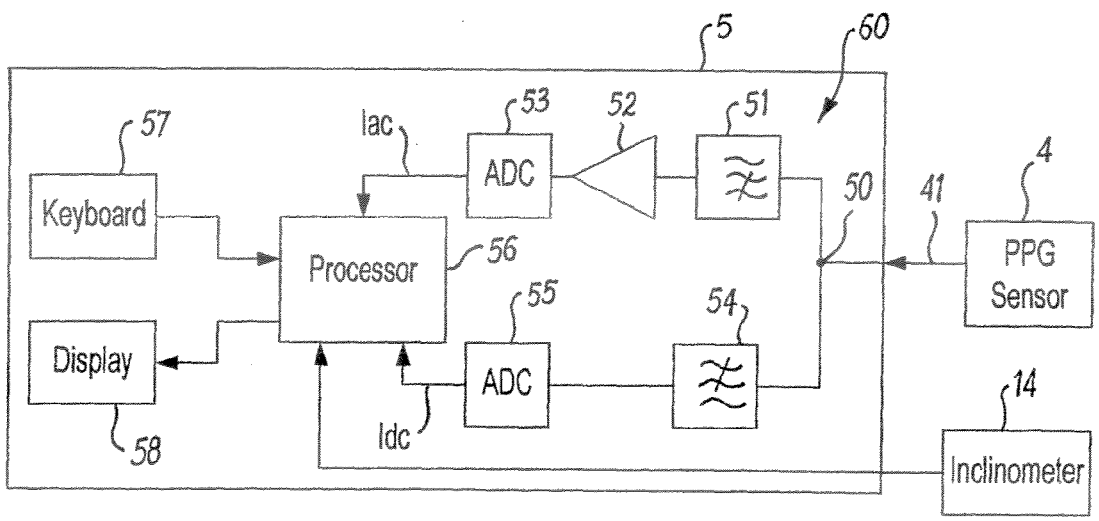
FIG. 3 schematically illustrates the components of the system illustrated in FIG. 2.

The PPG sensor 4 produces an output voltage that is dependent upon the intensity of the light detected by the sensor. This output voltage is provided to the pre-processing circuitry 60 of the electronic control unit 5 as illustrated in FIG. 3.

The pre-processing circuitry 60 includes an input node 50, a low pass filter 54, a high pass filter 52, a first analogue to digital converter (ADC) 55, a second analogue to digital converter (ADC) 53 and an amplifier 52.

The low pass filter 54 and high pass filter 51 are connected in parallel to the input node 50. The low pass filter 54 is connected in series to the first ADC 55 and the high pass filter is connected in series to the amplifier 52 which is connected to the second ADC.

The low pass filter 54 converts the sensor output 41 into a signal (Idc) that represents the steady-state or slowly varying intensity of the light detected by the PPG sensor 4. This signal is sampled and digitised by the second ADC and then provided to the processor 56.

The high pass filter 51 converts the sensor output 41 into a signal (Iac) that represents the varying intensity of the light detected by the PPG sensor 4. This signal is amplified by amplifier 52 and it is then sampled and digitised by the second ADC and then provided to the processor 56.

The low pass filter passes signals with a frequency less than ~1 Hz i.e. non-pulsating signals, whereas the high pass filter passes signals with a frequency of greater than ~1 Hz i.e. pulsating signals. The high pass signal Iac is therefore representative of the change of intensity caused by arterial pulses in the lower limb 12 of the subject. These cut-off frequencies may have to adapt, in practice, to individual heart rates.

The processor 56 processes the digitised signals Idc and Iac. It calculates a ratio of ratios R, $$R = \frac{I(\theta)_{AC}/I(\theta)_{DC}}{I(0)_{AC}/I(0)_{DC}}$$

where $I(\theta)_{ac}$ represents the varying intensity of the light detected by the PPG sensor 4 when the subject is in a first posture i.e. the lower limb is elevated with an incline of θ.

$I(\theta)_{dc}$ represents the steady state intensity of the light detected by the PPG sensor 4d when the subject is in a first posture i.e. the lower limb is elevated with an incline of θ.

$I(0)_{ac}$ represents the varying intensity of the light detected by the PPG sensor 4 when the subject is in a second posture i.e. the lower limb is elevated with an incline of 0 (zero).

$I(0)_{dc}$ represents the steady state intensity of the light detected by the PPG sensor 4 when the subject is in a second posture i.e. the lower limb is elevated with an incline of 0 (zero)

R will be unity if the blood volume pulsations remain unchanged as a proportion of the total blood volume when the limb is elevated. The ratio R can be used to categorise the postural response of the circulation system in the lower limb and foot.

For example, it might be the case that as the lower limb 12 is raised in a healthy arterial system Iac remains approximately constant but changes significantly for an unhealthy arterial system.

The value R represents a first perfusion indicator and it may be displayed on display 58.

Figure 4A:
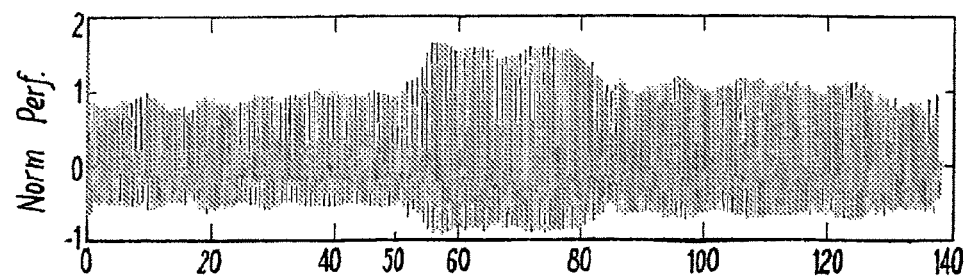
FIGS. 4A and 4B illustrate the change in pulsatile perfusion for a healthy subject's leg when raised to 30 degrees.

FIG. 4A illustrates the change in pulsatile perfusion for a healthy subject's leg when raised to 30 degrees. The subject was a 35 year old female. The Fig plots a trace of pulsatile perfusion i.e. $I_{AC}/I_{DC}$ on the Y-axis against time in seconds on the X-axis. The subject's leg is raised from 0 degrees elevation to 30 degrees elevation for 30 seconds between t=50 and 80 seconds. The plot of FIG. 4A may be displayed contemporaneously on the display 58.

Figure 4B:
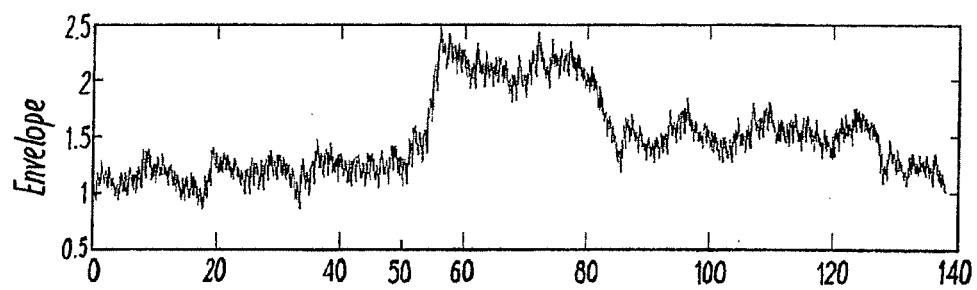

FIG. 4B illustrates the envelope of the trace in FIG. 4A. The plot of FIG. 4B may be displayed contemporaneously on the display 58.

The ratio R may be calculated from the ratio of pulsatile perfusion $(I(\theta)_{ac}/I(\theta)_{dc})$ when t=60 and pulsatile perfusion $(I(0)_{ac}/I(0)_{dc})$ when t=45. That is the ratio of the pulsatile perfusion soon after, but not immediately after, the leg has been raised to the pulsatile perfusion just before the leg has been raised. The ratio R for this healthy subject is in the region of 2. This indicates increased perfusion when the leg is elevated.

Figure 5A:
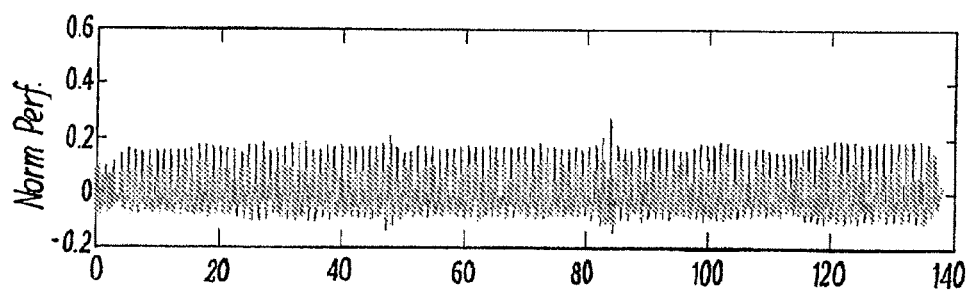
FIGS. 5A and 5B illustrate the change in pulsatile perfusion for an at risk subject's leg when raised to 30 degrees.

FIG. 5A illustrates the change in pulsatile perfusion for an at-risk subject's leg when raised to 30 degrees. The subject was a 79 year old diabetic male. The Fig plots a trace of pulsatile perfusion i.e. $I_{AC}/I_{DC}$ on the Y-axis against time in seconds on the X-axis. The subject's leg is raised from 0 degrees elevation to 30 degrees elevation for 30 seconds between t=50 and 80 seconds. The plot of FIG. 5A may be displayed contemporaneously on the display 58.

Figure 5B:
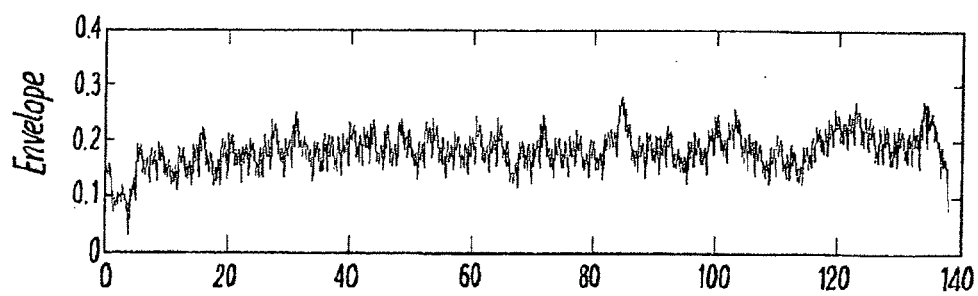

FIG. 5B illustrates the envelope of the trace in FIG. 5A. The plot of FIG. 5B may be displayed contemporaneously on the display 58.

The ratio R may be calculated from the ratio of pulsatile perfusion $(I(\theta)_{ac}/(\theta)_{dc})$ when t=60 and pulsatile perfusion $(I(0)_{ac}/I(0)_{dc})$ when t=45. That is the ratio of the pulsatile perfusion soon after, but not immediately after, the leg has been raised to the pulsatile perfusion just before the leg has been raised. The ratio R for this at-risk subject is in the region of 1. This indicates no change in perfusion when the leg is elevated.

The value of R indicates that the subject is at-risk of developing circulatory complications in the foot in extreme at-risk cases, the value of R may be less than 1.

A clinically determined threshold value T may be determined, such that when R for a particular subject is below the threshold, they are deemed at risk. This may be detected and displayed on the display 58. The extent of risk may also be calibrated against the difference between the threshold and calculated value of R and a quantitative or qualitative indication of the extent of risk may be displayed on the display 58.

The total output I of the PPG sensor 4 can be represented as Idc+Iac. The value of I is governed to a major extent by the blood volume illuminated and the skin absorption. The effect of skin absorption is removed by the ratio of ratios R. Because R is calculated, the actual light intensity used for a particular subject can vary according to what is required to obtain a well-resolved signal. This will be a function of many factors including skin type, thickness, anatomy, probe placement and probe coupling. Adjustment of the light intensity can be performed to optimise the signal acquisition with respect to the dynamic range of measurement.

The process of objective assessment of blood perfusion in a lower limb 12 of a subject involves the following steps. The subject rests in a supine position and an optically diffusive skin (ODS) 16 is placed over at least the subject's dorsum. The system 10 is then attached to the lower limb 12 using a strap. The approximate height of the subject is entered into the control unit 5 using the keyboard 57. The control unit 5 via the inclinometer 14 registers the base position (i.e. horizontal) and gives green light to proceed via display 58. The lower limb 12 of the subject is slowly raised and then held for a few seconds. The perfusion indicators are calculated and displayed.

Although the PPG sensor 4 is illustrated in FIG. 2 as a non-contact sensor, in alternative embodiments the sensor 4 may be attached to the lower limb, for example, by using an elasticated strap to hold the sensor 4 and control unit 5 in position during the test. The skin 16 also serves as a disposable hygiene barrier, reducing contamination of the sensors and cross infection between subjects.

The system 10 illustrated in FIGS. 2 and 3, may be simply adapted to determined a second perfusion indicator dependent upon the blanching of the skin tone of the lower limb 12 when it is elevated. This second perfusion indicator may be calculated in addition to or as an alternative to the first perfusion indicator R.

For example, a discrete spectrometer can be used to analyse the light reflected from the lower limb 12, when it is in the non-elevated position and when it is in the elevated position. The spectrometer can give a quantitative value for the blanching that occurs on elevating the limb.

As another example, the foot may be illuminated using IR light and also red light. An IR sensor's output may be pre-processed as described with reference to FIG. 3 to produce $I_{dc}[IR]$, $I_{ac}[IR]$. A red light sensor's output may be pre-processed as described with reference to FIG. 3 to produce $I_{dc}[red]$, $I_{ac}[red]$. The processor 56 may calculate a ratio $R'_{ac}$ or $R'_{ac}$ $$R'_{dc}=(I_{dc}[red](\theta)/(I_{dc}[IR](\theta)+I_{dc}[red](\theta)))/(I_{dc}[red](0)/(I_{dc}[IR](0)+I_{dc}[red](0)))$$

$$R'_{ac}=(I_{ac}[red](\theta)/(I_{ac}[IR](\theta)+I_{ac}[red](\theta)))/(I_{ac}[red](0)/(I_{ac}[IR](0)+I_{ac}[red](0)))$$

It should be appreciated that embodiments of the invention do not provide a diagnosis but provide an interim clinical indicator that will, for example, help in the assessment of the risks associated with a condition such as diabetes. The indicator indicates that something is wrong with the subject's circulation but not necessarily what is specifically wrong or what disease is the cause.

The previously described embodiments relate to a change in posture in which the limb at which measurement is made is elevated above the level of the subject's heart. However, more general postural changes are possible. For example, the position of the limb at which measurement is made may be simply changed between the first and second postures.

Such a change in position may be by raising the limb or lowering the limb and the limb need not be elevated above the heart level of the subject. Also, a postural change may arise from changing the position of a part of the subject's body at which measurement is not made. For example, the subject may change posture by bending from the torso while the limb at which measurement is made remains stationary.

Consequently a more general expression of the ratio of ratios R calculated by the processor 56 from the digitised signals Idc and Iac is:

$$R = \frac{I(1)_{AC}/I(1)_{DC}}{I(2)_{AC}/I(2)_{DC}}$$

where $I(1)_{ac}$ represents the varying intensity of the light detected by the PPG sensor 4 when the subject is in a first posture $I(1)_{dc}$ represents the steady state intensity of the light detected by the PPG sensor 4 when the subject is in the first posture $I(2)_{ac}$ represents the varying intensity of the light detected by the PPG sensor 4 when the subject is in a second posture $I(2)_{dc}$ represents the steady state intensity of the light detected by the PPG sensor 4 when the subject is in a second posture Although the preceding embodiments describe the limb at which measurement is made as a foot, the hand, lower arm or lower leg may also be suitable.

Although embodiments of the present invention have been described in the preceding paragraphs with reference to various examples, it should be appreciated that modifications to the examples given can be made without departing from the scope of the invention as claimed.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

The invention claimed is:

1. A method of assessing a subject by producing a subject-dependent indicator that measures a response of a subject's blood circulation system to postural change, comprising:
   providing a signal for a first posture dependent upon a blood volume in a limb of the subject when the subject is in a first posture by measuring a parameter indicative of the blood volume of the subject's limb when the subject is in the first posture prior to a postural change;
   providing a signal for a second posture dependent upon a blood volume in a limb of a subject after a change in subject posture from the first posture to a second posture, different to the first posture by measuring the parameter when the subject is in a second posture after the postural change;
   isolating at least a pulsating component of the measured parameter; and
   using a processor to calculate a quantitative subject-dependent indicator that measures a response of the subject's blood circulation system to the postural change and is dependent upon at least the pulsating component of the measured parameter for the first posture and the pulsating component of the measured parameter for the second posture.

2. A method as claimed in claim 1, further comprising:
   isolating a non-pulsating component of the measured parameter, wherein the quantitative indicator is dependent upon the non-pulsating component of the measured parameter of the signal for the second posture and the non-pulsating component of the measured parameter of the signal for the first posture.

3. A method as claimed in claim 2, wherein the limb is a foot.

4. A method as claimed in claim 1, wherein the position of the limb is changed between the first posture and the second posture.

5. A method as claimed in claim 1 wherein, in the first posture the limb is at a first elevation relative to the heart and in the second posture the limb is at a second different elevation relative to the heart.

6. A method as claimed in claim 1, wherein providing a signal for a second posture dependent upon a blood volume in a limb of a subject after a change in subject posture from the first posture to a second posture, different to the first posture comprises one of:
   providing a signal dependent upon a blood volume in the limb of the subject during an immediate response of the subject's blood circulation to the posture change;
   providing a non-steady state signal dependent upon a non-steady state blood volume in the limb of the subject after the posture change; and
   providing a signal dependent upon a blood volume in the limb of the subject less than 30 seconds after the posture change.

7. A method as claimed in claim 1, further comprising using the quantitative indicator to assess risk associated with a subject-dependent disease affecting the vascular system selected from the group comprising: diabetes, arteriosclerosis, Reynard's syndrome, and atherosclerosis.

8. A system that is configured to produce an indicator that measures a response of a subject's blood circulation to postural change, comprising:
   pre-processing circuitry configured to detect a signal for a first posture dependent upon a blood volume in a limb of the subject when the subject is in a first posture and is configured to detect the signal for a second posture dependent upon the blood volume in the limb of the subject after a change in the subject's posture from the first posture to a second posture, different to the first posture; and
   processing circuitry configured to calculate a quantitative indicator that quantifies a response of the subject's blood circulation to postural change and is dependent upon the signal for the first posture and the signal for the second posture, wherein the processing circuitry is configured to determine automatically when a posture change occurs.

9. A system as claimed in claim 8, further comprising a detector configured to detect postural change and provide a signal to the processing circuitry indicative of postural change.

10. A method of assessing a subject by producing a subject-dependent indicator that measures a response of a subject's blood circulation system to postural change, comprising:
    providing a signal for a first posture dependent upon a blood volume in a limb of the subject when the subject is in a first posture;
    providing a signal for a second posture dependent upon a blood volume in a limb of a subject after a change in subject posture from the first posture to a second posture, different to the first posture; and using a processor to calculate a quantitative subject-dependent indicator that measures a response of the subject's blood circulation system to the postural change and is dependent upon the signal for the first posture and the signal for the second posture, the method further comprising: determining automatically when a posture change occurs.

11. A method of assessing a subject by producing a subject-dependent indicator that measures a response of a subject's blood circulation system to postural change, comprising:

measuring a parameter indicative of the blood volume of the subject's limb when the subject is in a first posture prior to the postural change;

measuring the parameter when the subject is in a second posture after the postural change; and separating the parameter into a first component and a second component;

using a processor to calculate a quantitative subject-dependent indicator that measures a response of the subject's blood circulation system to the postural change, wherein the calculation takes as a first input value the first component of the parameter for the first posture, measured prior to the postural change, takes as a second input value, the first component of the measured parameter for the second posture, measured after the postural change takes as a third input value the second component of the parameter for the first posture, measured prior to the postural change, and that takes as a fourth input value, the second component of the measured parameter for the second posture, measured after the postural change.

12. A method as claimed in claim 11, comprising measuring a further parameter indicative of the blood volume of the subject's limb when the subject is in a first posture prior to the postural change;

measuring the further parameter when the subject is in a second posture after the postural change;

separating the further parameter into a first component and a second component;

wherein the calculation that takes as input values the first and second components of the measured parameter for the first posture, the first and second components of the measured parameter for the second posture, measured after the postural change; the first and second components of the further parameter for the first posture, and the first and second components of the measured further parameter for the second posture, measured after the postural change, wherein the parameter and further parameter are different optical parameters associated with different wavelengths of light.

* * * * *

UNITED STATES PATENT AND TRADEMARK OFFICE
CERTIFICATE OF CORRECTION

PATENT NO. : 9,730,590 B2
APPLICATION NO. : 14/049366
DATED : August 15, 2017
INVENTOR(S) : Crabtree et al.

It is certified that error appears in the above-identified patent and that said Letters Patent is hereby corrected as shown below:

On the Title Page

Item [30], "Jan. 8, 2005" should be deleted and --Jan. 8, 2004-- should be inserted.

Item [63], "Jan. 5, 2005" should be deleted and --Jan. 10, 2005-- should be inserted.

Signed and Sealed this
Thirty-first Day of October, 2017

Joseph Matal
*Performing the Functions and Duties of the*
*Under Secretary of Commerce for Intellectual Property and*
*Director of the United States Patent and Trademark Office*